United States Patent
Maraprygsavan et al.

(10) Patent No.: US 11,813,234 B2
(45) Date of Patent: Nov. 14, 2023

(54) USE OF CHLORITE TO TREAT RED BLOOD CELL DISEASES AND INDICATIONS MEDIATED THEREBY

(71) Applicant: OXO TRANSLATIONAL SCIENCE GMBH, Stadt Wanzleben-Börde (DE)

(72) Inventors: Paiboon Maraprygsavan, Samut Prakam (TH); Friedrich-Wilhelm Kuehne, Chiang Mai (TH)

(73) Assignee: OXO TRANSLATIONAL SCIENCE GMBH, Stadt Wanzleben-Börde (DE)

( * ) Notice: Subject to any disclaimer, the term of this patent is extended or adjusted under 35 U.S.C. 154(b) by 0 days.

(21) Appl. No.: 15/753,516

(22) PCT Filed: Aug. 22, 2016

(86) PCT No.: PCT/IB2016/055011
§ 371 (c)(1),
(2) Date: Feb. 19, 2018

(87) PCT Pub. No.: WO2017/029648
PCT Pub. Date: Feb. 23, 2017

(65) Prior Publication Data
US 2018/0243334 A1 Aug. 30, 2018

Related U.S. Application Data

(60) Provisional application No. 62/207,774, filed on Aug. 20, 2015.

(51) Int. Cl.
| | | |
|---|---|---|
| A61K 33/20 | (2006.01) | |
| A61K 33/00 | (2006.01) | |
| A61K 33/14 | (2006.01) | |
| A61P 3/10 | (2006.01) | |
| A61P 7/06 | (2006.01) | |

(52) U.S. Cl.
CPC ............ *A61K 33/20* (2013.01); *A61K 33/00* (2013.01); *A61K 33/14* (2013.01); *A61P 3/10* (2018.01); *A61P 7/06* (2018.01)

(58) Field of Classification Search
CPC ........ A61K 33/20; A61K 33/00; A61K 33/13; A61P 3/10; A61P 7/06
See application file for complete search history.

(56) References Cited

U.S. PATENT DOCUMENTS

| | | | |
|---|---|---|---|
| 8,252,343 B2 | 8/2012 | Brosz et al. | |
| 2010/0282607 A1* | 11/2010 | Oishi | G01N 27/44747 204/450 |
| 2011/0118180 A1* | 5/2011 | Silvestre | A61K 31/155 514/6.9 |
| 2012/0134929 A1* | 5/2012 | McGrath | A61P 1/02 424/9.2 |
| 2013/0177629 A1* | 7/2013 | Martin | A61K 9/0019 424/450 |
| 2014/0287064 A1* | 9/2014 | Swenholt | A61K 36/63 424/665 |

FOREIGN PATENT DOCUMENTS

| | | |
|---|---|---|
| JP | 2001518512 A5 | 1/2006 |
| JP | 2013501046 A | 1/2013 |
| JP | 2015502400 A1 | 1/2015 |
| WO | 2001040517 A2 | 6/2001 |
| WO | 2004028469 A2 | 4/2004 |
| WO | 2013109949 A1 | 7/2013 |
| WO | 2015175974 A1 | 11/2015 |

OTHER PUBLICATIONS

Koransky, Pharmakologie (1952), 215, pp. 483-491 (Abstract, STN online, file CAPLUS). (Year: 1952).*
NGSP:Factors that Interfere with HbA1c Test Results (2010) (updated Apr. 19, 2019) (obtained online on Sep. 30, 2019) <http://www.ngsp.org/factors.asp.>. (Year: 2019).*
Mark J. Koury, Abnormal erythropoiesis and the pathophysiology of chronic anemia,Blood Reviews, vol. 28, Issue 2, pp. 59-66. (Year: 2014).*
Couri, D., et al., "Toxicological Effects of Chlorine Dioxide, Chlorite and Clorate." Environmental Health Perspectives, 1982, 46: 13-17.
Kandhare, A.D., et al., "Naringin, a flavanone glycoside, promotes angiogenesis and inhibits endothelial apoptosis through modulation of inflammatory and growth factor expression in diabetic foot ulcer in rats." Chemico-Biological Interaction, 2014, 219: 101-112.

(Continued)

*Primary Examiner* — Abigail Vanhorn
(74) *Attorney, Agent, or Firm* — SALIWANCHIK, LLOYD & EISENSCHENK

(57) ABSTRACT

Method of treating hyperglycemia induced Red Blood Cell Disease/Dysfunction (RBCD) caused by generation of early and late glycation end products. Method of treating hemolytic anemia, smoldering hemolytic anemia, sickle cell anemia, hemorrhagic diseases, hemorrhagic stroke, hemorrhagic bleeding. Method of treating RBCD to prevent progression to diabetes associated vascular complications referred to as Syndrome X, particularly to prevent progression to chronic kidney disease, coronary vascular disease, and peripheral vascular disease.

23 Claims, 5 Drawing Sheets

(56) References Cited

OTHER PUBLICATIONS

Ueno, H., et al., "Hematological Effects of Chlorine Dioxide on In Vitro Exposure in Mouse, Rat and Human Blood and on Subchronic Exposure in Mice." Journal of Health Science, 2000, 46(2): 110-116.

Yingsakmongkol, N., et al., "Effect of WF10 (Immunokine) on Diabetic Foot Ulcer Therapy: A Double-blind, Randomized, Placebo-controlled Trial." The Journal of Foot & Ankle Surgery, 2011, 50: 635-640.

International Search Report WO2016IB55011A dated Feb. 20, 2018 (pp. 1-21).

Narongchai Yingsakmongkol et al: "Effect of WF10 (Immunokine) on Diabetic Foot Ulcer Therapy: A Double-blind, Randomized, Placebo-controlled Trial", Journal of Foot and Ankle Surgery, vol. 50, No. 6, 2011, pp. 635-640, XP028327260, ISSN: 1067-2516, [retrieved on May 19, 2011], DOI: 10.1053/J.JFAS.2011.05.006 (abstract).

Paiboon Maraprygsavan et al: "The chlorite-based drug WF10 constantly reduces hemoglobin A1c values and improves glucose control in diabetes patients with severe foot syndrome", Journal of Clinical & Translational Endocrinology, vol. 4, Jun. 1, 2016 (Jun. 1, 2016), pp. 53-58, XP055319264, ISSN: 2214-6237, DOI: 10.1016/j.jcte.2016.05.001.

\* cited by examiner

WF10 strongly and consistently reduces HbA1c percentage into normal range

A.) One cycle (5 consecutive infusions on day 1, 2, 3, 4, 5) of WF10 were administered to 7 patients (5 male, 2 female) with anemia and severe diabetic foot ulcer. HbA1c declined during treatment from a mean of 9.3 % high risk into low risk range.

FIG. 1B

| Patient | HbA1c % | | | Reduction of HbA1c | |
|---|---|---|---|---|---|
| | Baseline | After 4wk | After 8wk | After 4 wk | After 8 wk |
| AS | 11.5 | 4.8 | 5.4 | -6.7 | -6.1 |
| KP | 8.9 | 6.2 | 6.4 | -2.7 | -2.5 |
| NT | 9.7 | 5.5 | 5.3 | -4.2 | -4.4 |
| PP | 9.2 | 7.8 | NA | -1.4 | NA |
| NP | 7.7 | 6.5 | 5.2 | -1.2 | -2.5 |
| UT | 6.9 | 5.1 | 5.1 | -1.8 | -1.8 |
| PS | 11.1 | 6.8 | 5.5 | -4.3 | -5.6 |
| mean | 9.3 | 6.1 | 5.5 | -3.2 | -3.8 |

NA: Not Available

B.) Mean HbA1c percentage at baseline = 9.3%, at week 4 = 6.1%, at week 8 = 5.5.%. Every 1% drop in HbA1c reduces the risk for micro vascular complications by 40%, and risk for death by 21% (NaRCAD 2013).

Plotted anemia values hemoglobin and hematocrit before and after; baseline: 30% Hct, week 12: 36% Hct

FIG. 3

| Patient | HbA1c % | | | Reduction of HbA1c | |
|---|---|---|---|---|---|
| | Baseline | After 4wk | After 8wk | After 4 wk | After 8 wk |
| AS | 11.5 | 4.8 | 5.4 | -6.7 | -6.1 |
| KP | 8.9 | 6.2 | 6.4 | -2.7 | -2.5 |
| NT | 9.7 | 5.5 | 5.3 | -4.2 | -4.4 |
| PP | 9.2 | 7.8 | NA | -1.4 | NA |
| NP | 7.7 | 6.5 | 5.2 | -1.2 | -2.5 |
| UT | 6.9 | 5.1 | 5.1 | -1.8 | -1.8 |
| PS | 11.1 | 6.8 | 5.5 | -4.3 | -5.6 |
| mean | 9.3 | 6.1 | 5.5 | -3.2 | -3.8 |

NA: Not Available

B.) Mean HbA1c percentage at baseline = 9.3%, at week 4 = 6.1%, at week 8 = 5.5.%. Every 1% drop in HbA1c reduces the risk for micro vascular complications by 40%, and risk for death by 21% (NaRCAD 2013).

First patient with insulin resistance in which decline of fasting sugar had been observed (historic)

E11.5 Non-insulin-dependent diabetes mellitus with peripheral circulatory complications Underlying Diseases 179.2 Peripheral angiopathy in diseases classified elsewhere E87.6 Hypokalaemia

USE OF CHLORITE TO TREAT RED BLOOD CELL DISEASES AND INDICATIONS MEDIATED THEREBY

CROSS REFERENCE TO RELATED APPLICATIONS

This application is a national phase filing under 35 U.S.C. § 371 of International Application No. PCT/IB2016/055011 filed Aug. 22, 2016, which claims priority from U.S. Provisional Application Ser. No. 62/207,774, filed Aug. 20, 2015, the entire contents of which are hereby incorporated by reference herein.

FIELD OF THE INVENTION

The present invention relates to a method of treating hyperglycemia induced Red Blood Cell Disease/Dysfunction (RBCD), caused by generation of early and late glycation endproducts (AGE), and indications related to RBCD and associated pathologies/indications mediated thereby. RBCD includes hemolytic anemia, smoldering hemolytic anemia, hemorrhagic diseases, hemorrhagic events, hemorrhagic bleeding.

The present invention enables treatment of RBCD caused by early glycation. RBCD in diabetes is biochemically quantified by generation of the early glycation product HbA1c, and morphologically characterized by loss of discoid shape and deformability of RBC.

More particularly the present invention relates to the use of chlorite solutions such as WF10 or for such treatment.

BACKGROUND OF THE INVENTION

The Red Blood Cell (RBC) or erythrocyte is the most common type of blood cell and is a vertebrate organism's principal means to deliver oxygen to its tissue. Additionally their task is to produce energy. RBC's of healthy individuals are very robust cells without a nucleus and exert a 'beautiful' discoid shape. About 30% of all human cells are RBC. The RBC is called erythrocyte. Every second 2-3 Mill new erythrocytes are produced and the same figure discharged.

New generated reticulocytes from the bone marrow mature within days to robust and healthy erythrocytes. Under chronic hyperglycemia or glycemic variability a non-enzymatic reaction between open ring sugar aldehyde groups and amino groups of erythrocyte proteins, takes place, called 'early glycation'. These products are named after its discoverer French Chemist Louis-Camille Maillard. The best defined early glycation product is Hemoglobin A1c. HbA1c is a subfraction of hemoglobin with a N-terminal valine on the beta chain of hemoglobin. Over a course of days to weeks, early glycation products undergo further reactions (Amadorri rearrangements named after Italian Chemist Amadori) leading to 'advanced glycation end' products (AGE, Norge 1989, Yamagishi 2012). Elevated early and late glycation products render the erythrocyte dysfunctional, sick. Those erythrocytes demonstrate increased mechanic fragility and are less robust, the discoid shape changes to a skewed morphology and a disturbing/dangerous rheology (Pretorius/Lippi, SEM, AFM).

These erythrocytes have lost the capability to carry oxygen (only erythrocytes with metabolites in the ferrous state ($Fe^{2+}$) can carry oxygen), and entertain a smoldering intracellular and intravascular hemolysis with freeing and releasing free ferric($Fe^{3+}$) hemoglobin and $Fe^{4+}$protophorphyrin IX/hemin into the vasculum where it attach to vessel wall and creates havoc. These dysfunctional erythrocytes and their released cytotoxic hemoglobin species are the origin of harmful diabetes associated pathologies.

The present invention will identify those sick and dysfunctional erythrocytes as a therapeutic target. The present invention will significantly reduce 12-month mortality and major amputations of DFU disease, it will stabilize/improve kidney function, and will reduce other diabetes associated pathologies (recently referred to as Syndrome X).

The penetration of glucose into human red blood cells are readily distinguishable from passive permeation (Hajjawi, O. S. 2013) In hyperglycemia glucose uptake by erythrocytes is unrestricted and regulated only by the level of intravascular plasma glucose and glucose utilization. The glucose uptake by erythrocytes (via glucose uptake receptors Glut 1) is independent from insulin. Insulin dependent cells are mainly hepatocytes, muscle cells, and fat cells bearing the uptake receptor GLUT4. Excessive administration of insulin and stringent oral anti-diabetes drug as mono or combination therapy are capable to control fasting sugar but cannot inhibit the glucose uptake in erythrocytes and endothelial cells under hyperglycemia nor can it prevent generation of early and late glycation end products.

The generation of early (HbA1c) and advanced glycation end products (AGE) in erythrocytes creates intracellular hemolytic smoldering with generation of very toxic hemoglobin metabolites, mainly in the $Fe^{4+}$ state, such as protophorphyrin IX (called hemin).

Insulin is not in a position to prevent the production of AGE or diminish harmful hemoglobin metabolites and by that to restore healthy erythrocyte function.

Currently no such approach is in sight.

The new invention provides a treatment for 'clearance' of all dysfunctional RBC's in a first step from the blood of diabetes patients and in a second step the invention diminish immediately all harmful metabolites. In patients with long-term hyperglycemia this can go along with a transient drop in hematocrit which dependent from the amount of dysfunctional RBC's. Additionally the present invention provides a method of diminishing hemolytic smoldering, by this reaction it prevents 'reinfection' of new red blood cells just 'born' by erythropoiesis, with discoid shape and intact morphology. Without a therapeutic 'clearance' on day one and subsequent scavenging over a certain period (1 to 5 days) a progression to harmful pathologies is not halted.

As long as free hemoglobin/hemin disease entertains a smoldering intracellular hemolysis with a transfer of this disease to the newborn reticulocytes and permanently consuming nitric monoxide the extracellular havoc in the capillaries leading to ischemia is not halted.

By smoldering hemolysis is meant a state where the true extent of the reduced redox state and of anemia is covered and only when the dysfunctional RBCs are cleared can the true extent of hemolysis be seen. Without clearance no induction of erythropoiesis and recovery of RBCs and no interruption of the destruction of young cells from bone marrow (reticulocytes) is seen. Smoldering thus means generation of hemolytic metabolites before burst. These are RBCs in a reduced redox state ($Fe^{3+}$ and $Fe^{4+}$).

This treatment goes along with rapid decrease of fasting sugar and normalizing HbA1c values. Creatinine values remain stable and 'estimated Glomerular Filtration Rate' (eGFR) increases. It reduces high platelet counts into a normal range. High platelets counts in hyperglycemia are an early predictor for nephropathy.

Within 5-6 weeks after the first infusion the anemia lessened and hematocrit values were higher then at baseline.

Currently available evidence-based treatments focus mainly on sugar control. Optimal regimens can improve outcome as follow:

In 'The diabetes epidemic and its impact on Thailand' (Deerochanawong, C., 2013) diabetes is defined by a 'failure of the pancreas to produce insulin or to produce and utilize sufficient insulin to keep blood glucose under control'.

Current academic knowledge and clinical experience teach that stringent glucose control is imperative to prevent disease progression to 'secondary complications and death'.

Secondary complications of diabetes are defined as coronary artery disease (CAD), peripheral artery disease (PAD), chronic kidney disease (CKD) or insufficiently, retinopathy (RN), neuropathy, diabetic foot ulcer (DFU), stroke, which altogether are recently referred to as 'Syndrome X'.

There is evidence-based consensus that a decrease in every 1%-point drop of HbA1c will reduce long-term complications as follows: 43% in lower limb amputation or fatal peripheral vascular disease, 37% in micro vascular disease, 30% in heart failure and myocardial infarction together, and 12% in stroke. (See graph from Thailand Diabetes Report 2013). It urges therefore the need for stringent glucose control by all means, and emphasizing the extensive use of different forms of insulin.

But these recommendations seem to be wrong: worldwide diabetes mellitus is on the rise and so the number of complications/pathologies. Based on the assumption that stringent and aggressive sugar control would decrease the number of complications only 11% of complications in Diabetes Type 1 could be explained by such an aggressive therapy, and in diabetes Type 2 even less. This is the result of recently conducted large human trials (Nawroth 2016). Furthermore this large trials also reveal a higher risk for cardiac arrest, stroke, and death (Nawroth 2016).

Interestingly a 3-fold increase of insulin administration in Malaysian patients from 2009 to 2012 has not resulted in mean HbA1c decline (Malaysia National Report on Diabetes 2013). The number of patients bearing high percentage of HbA1c (<8% and <10% HbA1c) increased despite doubling insulin administration (74% of diabetes patients in 2009 compared to 76.9% in 2012). Evermore classical glucose control medications (Metformin, Sulphonylurea, Alpha-Glucosidase Inhibitors, Meglitinides, Glitazones, Insulin) seem to be less successful in this group of patients with already high HbA1c percentage.

Taken together there are many treatment regimens able to reduce HbA1c levels up to 1% but the number of patients showing HbA1c levels above 8% is on the rise. A substantial decline in HbA1c from baseline over 8% seems to be an exception.

As stringent glycemic control seem to be mandatory there is an urgent need for treating the origin for diabetes derived pathologies. This origin is independent from insulin. There is an urgent need for a radical new treatment approach targeting another segment of cells bearing the glucose transporter receptor GLUT 1 with the objective to stop the spread of the diabetes epidemic and to halt the rising cost for the healthcare system.

The Red Blood Cell (and the endothelial cell) is the new target.

Anemia is commonly associated with hyperglycemia but currently not listed as diabetes associated pathology or part of Syndrome X.

Although molecular details of the pathogenesis of Syndrome X (CAD, PAD, CKD, RN, Neuropathy, DFU) are very complex and to our current knowledge not connected to erythrocyte dysfunction, reactions of open-ring form of glucose with different targets provide the basis for these pathologies.

In biological fluids, glucose exists predominantly in the unreactive ring form that is in equilibrium with the open-ring form, which bears a reactive aldehyde group. Aldehydes are known to interact easily with molecules bearing amino groups.

These reactions include the formation of intermediate Schiff's bases and further transformations like Amadorri rearrangements. In this way, glucose molecules become attached to proteins and other biological targets. Evidently, these posttranslational transformations of biological materials increase considerably under hyperglycemia. Collectively, the products of these transformations are summarized as 'advanced glycation end' (AGE) products (Njoroge et al).

One special example of these reactions is the formation of hemoglobin forms bearing glycated side chains. HbA1c is a sub fraction of hemoglobin with a glycated N-terminal valine on the beta-chain of hemoglobin A1, a parameter which is widely used nowadays as undisputed marker for lasting sugar control over the lifetime of erythrocytes (120 days).

Hemoglobin A1c (HbA1c) level represents an early glycation product and the degree of 'advanced glycation end' product's (AGE) and correlates strongly with anemia and risk of end-organ damage including renal insufficiency, visual impairment, and neuropathy. Most prominently it correlates with death.

Every 1% drop in HbA1c reduces the risk of micro vascular complications by 40% and the risk of death by 21%. (Graph from NaRCAD 2013)

If HbA1c values is over 6.5% it is commonly called 'hyperglycemic' reflecting mild risk, if HbA1c is over 8.5% it is commonly referred to as 'insulin resistant' and reflects a high risk clinical condition associated with morbidity and mortality.

If HbA1c percentage is permanently measured below 6.0% the risk to progress to Syndrome X should be dramatically reduced.

Despite introduction of lifestyle changing programs, old and new oral anti-diabetes medications, and substantial substitutive insulin titration for blood glucose control, millions of diabetes patients still express increasing HbA1c values reflecting limited therapeutic effects of the current available therapy regimens (mono or combined treatment) with the focus on glucose control.

These millions of patients are prone for developing severe pathologies and are the cause of the most costly burden for our health care system as Diabetes Mellitus became endemic (25 Million in USA, 4 Mill in Thailand, 300 Mill worldwide).

There is an urgent medical need for a new treatment approach beside glucose control, with a focus on restoring glucose utility in insulin independent cells.

Currently no therapy exist to halt progression of hyperglycemia to secondary complications and death by drastically reducing HbA1c percentage—or even to reverse the destiny of chronic hyperglycemia. There are currently 1289 studies undertaken worldwide with the objective to better control glucose, 41 of these studies alone in Thailand. The endpoint in all of these studies is the degree of lowering HbA1c.

None of this studies focus on treatment of Red Blood Cell dysfunction by clearance of sick and dangerous erythrocytes and with the objective to diminish harmful smoldering of intracellular hemolysis and intravascular havoc (attached hemin to vessel wall).

Treatments leading to normal range of HbA1c (<6.0% HbA1c) will eliminate the risk to develop Syndrome X.

Such a treatment does currently not exist.

This invention provides a method to treat Red Blood Cell dysfunction as the origin of Syndrome X. The treatment will not only restore healthy RBC function and morphology, but also reduce anemia and improve kidney function. After initial treatment the HbA1c percentage will be in a range like those of healthy individuals, independent from baseline percentage. In one of 7 cases treated with WF10 in 2015 and presented in this patent a second treatment cycle has been given for osteomyelitis resolution (FWK).

None of these studies focus on treatment of Red Blood Cell dysfunction with the objective to diminish harmful smoldering intracellular hemolysis and intravascular havoc. The discovery of glucose uptake receptors has shown that only 3 types of cells are insulin dependent bearing the glucose uptake receptor GLUT 4, these are hepatocytes, muscle cells, and fat cells. The glucose uptake by these cells is regulated by insulin (a hormone produced in the beta cells of the pancreas), therefore these cells are called 'insulin dependent cells', or 'insulin dependent storage'.

Successful treatment of diabetes requires a persistent approach in life style modification (nutrition and exercise) and in best cases can reduce HbA1c by 0.3%. But most patients will develop HbA1c values above 7% because the natural course of diabetes is a progressive loss of insulin sensitivity and production. Current therapy regimens of oral anti-diabetics (OAD) and insulin have to be administered daily to achieve specific HbA1c targets. Newer non-insulin medications as add on to Metformin etc might lower HbA1c by 0.5-1% but do not have shown evidence for inhibition of generation of AGE nor reduction of actual end-organ damage and might not be able to do so based on currently known scientific approaches.

There is also urgent need for shorter medical treatment approaches with long lasting therapeutic effects replacing a daily treatment regimen.

These 'insulin independent' cells are predominantly red blood cells, mesangial cells in capillary of the glomerulus, nerve and Swann cells. These cells bear the glucose uptake receptors GLUT-1 and Glut-3. The most important ones are evidently the erythrocytes representing more then 25% of all human cells.

The erythrocytes have to our current knowledge not been implicated as key cells in the origin of end-organ damage. It will be shown that that treatment of DFU are closely associated with detoxification of free hemoglobin forms and the bioavailability of nitric monoxide and blood circulation based on restored rheology and shape of RBC.

This invention identifies the disastrous effect of RBCD as the origin of intracellular/extracellular hemolysis spreading to the vascular endothelium and the kidney.

A treatment method will be provided eliminate sick erythrocytes and to diminish efficiently the yield of cytotoxic hemoglobin metabolites that might appear after excessive hemolysis of red blood cells under pathologic conditions. Only an effective and rapid scavenging of these metabolites (protecting haptoglobin and hemopexin are exhausted over time) will drastically reduce the origin for secondary complications. One other major point here is to inactivate these very reactive hemoglobin derivatives as competitive target for nitric oxide.

Glucose exists predominantly in the nonreactive ring form, which is in equilibrium with the open ring form, the latter bearing a reactive aldehyde group. Aldehydes react easily with proteins bearing amino groups.

One special example is the generation of the early glycation product (hemprotein) A1c (HbA1c), the most abandoned protein in red blood cells.

The glycation of hemproteins is the starting point of intracellular hemolysis in erythrocytes and the origin of smoldering hemolytic anemia. The extent of glycation is measured by HbA1c. The extent of anemia is measured by hematocrit.

Patients with HbA1c values above 8% have usually 25% hematocrit reduction reflecting substantial anemia.

Long-term hyperglycemia and the correlating hemolytic anemia is a harmful condition to our organism associated with numerous tissue and organ-end damage.

These diseases are progressively developing on the basis of a disturbed blood circulation and a reduced ability to translate electrical signals in nerves (Arnhold).

One classical example of those diseases and by far the most progressed complication referred to as Syndrome X is the diabetic foot (DFU).

This complication is progressively developing on the basis of a disturbed blood circulation and reduced ability to translate electrical signals in nerves. Increased glycation of proteins in blood, endothelial and other cells, diminished osmotic stability of RBC, and a reduced redox state of RBC, and finally a higher degree of hemolysis, contribute to this harmful pathology with a staggering 12-month mortality of 16.7% (Insurance Medicine). The 12-month mortality in DFU is higher then in most cancers. After major amputation the 12-month mortality doubles to over 30%.

The prevalence of diabetic microvascular complications and diabetic neuropathy is also reported to be higher in patients with poor glycemic control. It has been strongly shown that HbA1c is a significant risk factor for overall amputation in previous studies. HbA1c was a predictive factor for risk of amputation, and the cutoff point for the risk is 9.2% (specificity 81% and sensitivity 87.5%).

Mortality in a retrospective study of 192 patients with DFU and 306 patients treated overall (study patients with severe infected, neuropathic, and ischemic diabetic ulcers were treated, 12 month mortality was recorded from patients file and compared to international documented mortality: 1.55% 12 months mortality in 192 study patients, and 3.92% 12-month-mortality in 306 patients overall compared to 16.7% 12-month-mortality reported in 'Insurance Medicine')

Enhanced intracellular glucose levels in RBC favor also the conversion of glucose into sorbitol via aldose reductase (Gugliucci, 2000, Brownlee, 2005). During this reaction, which represents the first step in the polyol-pathway, NADPH is oxidized to NADP+. In the pathogenesis of diabetes, this reaction is also important in capillary endothelial cell in retina, mesangial cell in the renal glomerulus, and neurons and Swann cells of peripheral nerves where glucose uptake is insulin independent. Consequently high intracellular glucose depletes NADPH and reduces values of nitric monoxide, glutathione, and others. All this metabolites require NADPH for their synthesis. It becomes clear that intensification of the polyol pathway creates havoc in those cells, particularly the RBC.

Sorbitol does not freely permeate through cell membranes and accumulation creates osmotic stress in RBC. RBC contains also aldose reductase. The activity of this enzyme is regulated by nitric monoxide (Chandra et al 2002, Srivastava 2003). Normal level of nitric oxide depress its activity and in healthy erythrocytes only 3% of total glucose is metabolized into sorbitol. With decreased bioavailability of nitric monoxide the activity of aldose reductase rises considerably and up to 30% of glucose is converted into sorbitol. This has fatal consequences for the increased mechanic fragility of erythrocytes (Lippi 2011). In fact fasting plasma glucose is the strongest correlate of increased mechanical fragility of erythrocytes and anemia. And last but not least osmotic stability and morphological integrity of erythrocytes negatively correlates with increasing HbA1c values (Kung 2009).

Taken together there is a clear relationship between hemolysis degree on one side and HbA1c values on the other side in hyperglycemic patients.

There is thus an urgent medical need for a new therapeutic approach to address the RBCD with smoldering intracellular hemolysis.

While it is known that DFU could be treated with WF-10 (Yingsakmongol, Journal of Wound Care, "Clinical Outcomes of WF-10 adjunct to standard treatment of Diabetic Foot Ulcers," Aug. 16, 2013, hereby incorporated by reference; Yingsakmongol et al., jfas November-December 2011, Vol. 50, Issue 6, pp. 635-640, hereby incorporated by reference the mechanism by which improvement was seen, addressing RBCD, was not known and consequently it was not known or apparent to employ chlorite-containing compositions to treat diabetes per se nor other diabetes-related complications, particularly in patients who do not exhibit DFU.

SUMMARY OF THE INVENTION

In one aspect the present invention provides a method of treating red blood cell disease/dysfunction and early glycation using a composition containing chlorite ions ($ClO_2^-$), particularly hyperglemia induced red blood cell disease/dysfunction using said composition.

Stabilized solutions of chlorite ions are known in the art, e.g., in U.S. Pat. No. 8,252,343 and Application No. 2011/0076344, whereby incorporated by reference for such disclosures.

In an alternative aspect the present invention provides a method to restore a healthy red blood cell function in hyperglycemic patients by normalizing hemoglobin A1c.

In an alternative aspect the present invention provides a method of reducing diabetes associated complications referred to as Syndrome X or to halt progression of those pathologies.

In an alternative aspect the invention provides a method to halt progression to chronic kidney disease or reverse the destiny.

In an alternative aspect the present invention provides a method to scavenge cytotoxic metabolites from hemoglobin thereby efficiently diminishing RBCD.

In an alternative aspect the present invention provides a method for the inhibition, inactivation, reduction, prevention or treatment of hemolytic anemia like symptoms comprising administering to a patient suffering from anemia or hemorrhagic symptoms a therapeutically effective amount of a composition containing chlorite ions.

In an alternative aspect the present invention provides a method to scavenge hemoglobin meatbolites in hemorrhagic diseases.

In an alternative aspect the present invention provides a method to treat Rhabdomolysis.

The invention further provides a method to treat diabetes, and/or lower HbA1C. and/or treat diabetes-related kidney insufficiency, diabetes related coronary artery disease, diabetes-related peripheral artery disease, diabetes-related retinopathy or diabetes-related neuropathy.

BRIEF DESCRIPTION OF THE DRAWINGS

The present invention will be described in further detail below with reference to the accompanying drawing in which:

FIGS. 1A-1B are of a graph and table showing blood analysis of HbA1c percentage in 7 patients at baseline, week 4, week 8. WF10 was infused in a dose of 0.5 ml/kg per day for 5 consecutive days in 500 ml saline over 4-6 hours. A) All values after 4 and 8 weeks are in the normal range <6.5% HbA1c. B) Mean values declined from 9.8% to 5.4% after 8 weeks.

FIG. 3 is a graph of one typical biochemical scenario after WF10 infusion: HbA1c decline, fasting sugar decline, creatinine decline, hematocrit increase over time in a patient having diabetes Typ 2. (Slide will follow)

DETAILED DESCRIPTION OF THE INVENTION

Figure 1A:
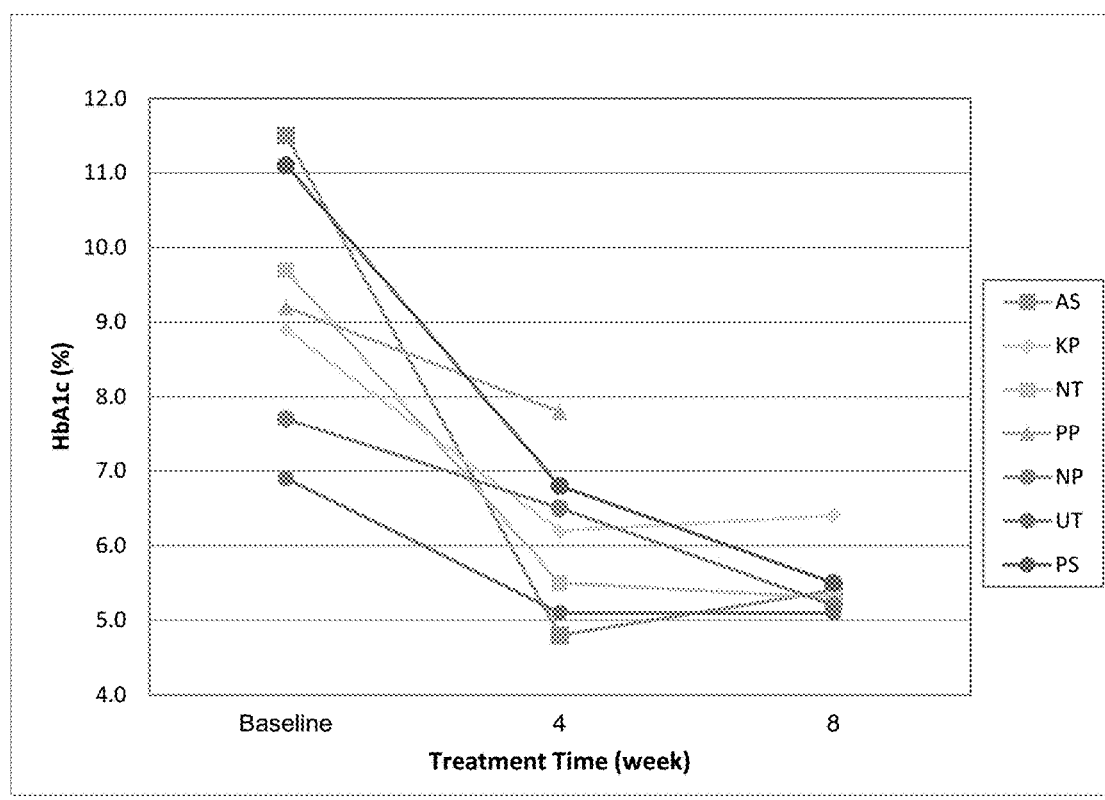
Figure 2:
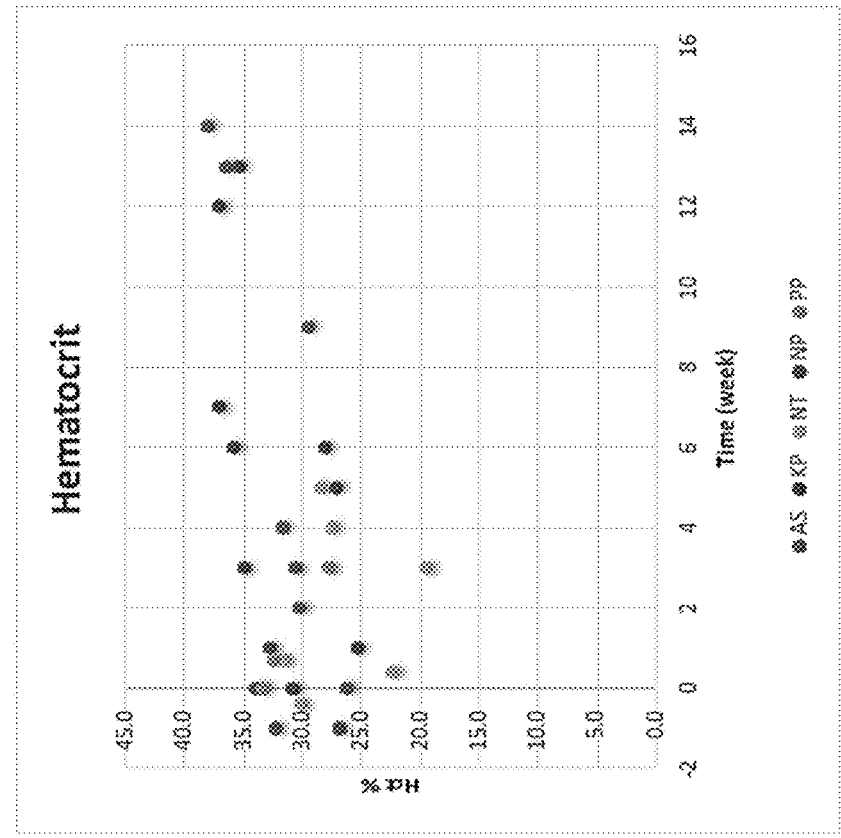
FIG. 2 is a graph showing evidence-based treatment can improve outcome: every 1% drop in HbA1c reduces the risk of microvascular complications by 40%, and death by 21%.
Figure 2:
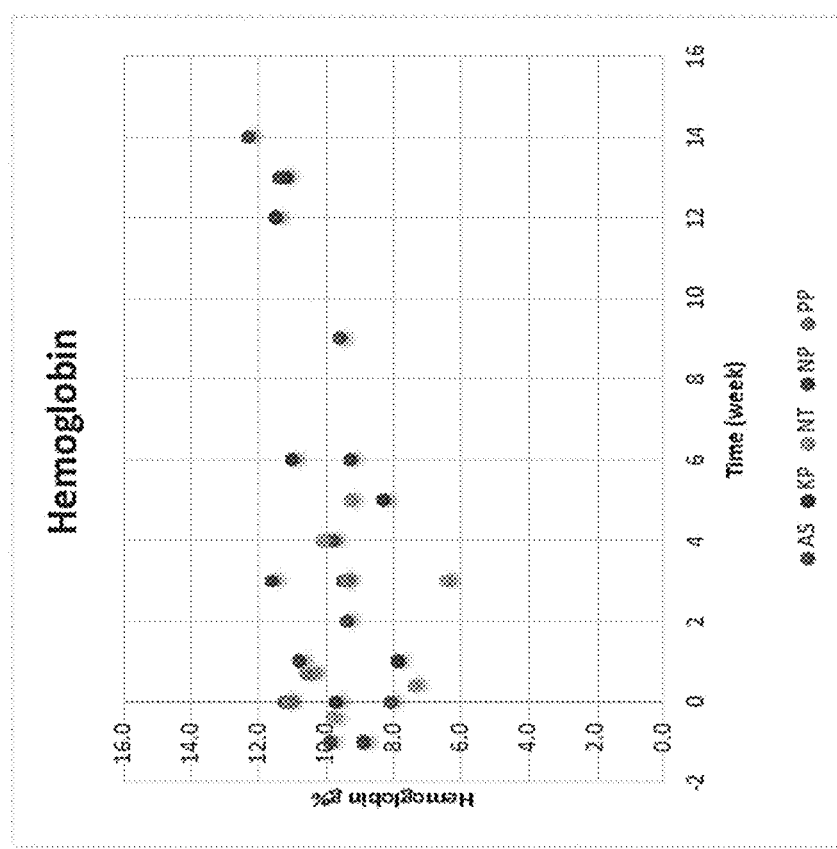
Figure 4:
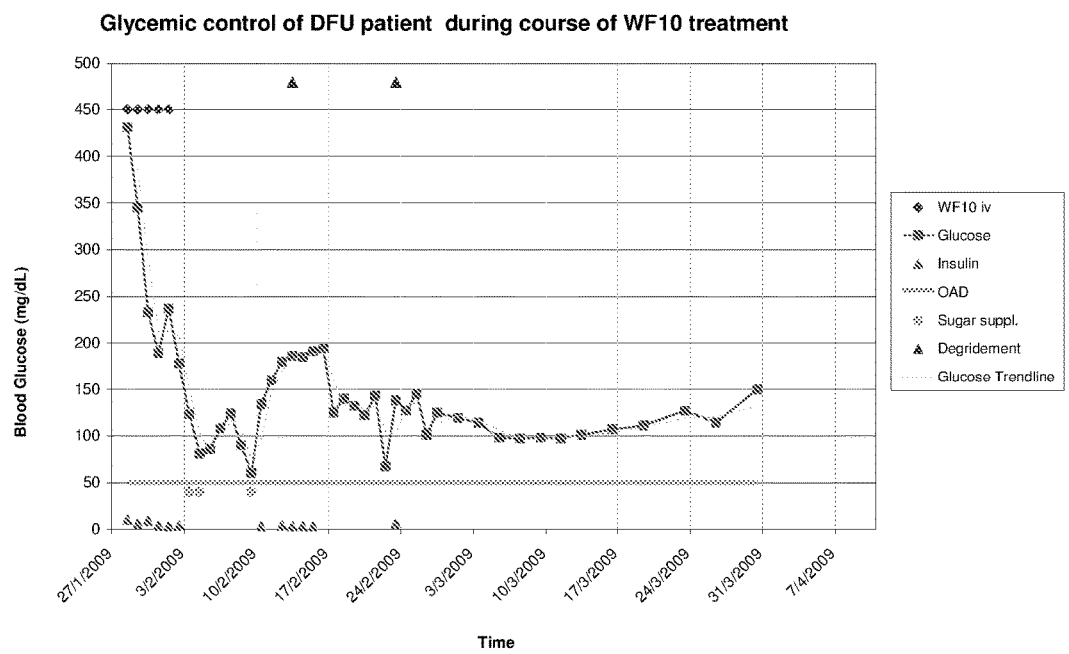
FIG. 4 is a graph showing the fasting sugar decline from over 400 mg/dl to around 120 mg/dl after 5 consecutive infusions with WF10. This patient had a 20 year history of diabetes Typ 2, was insuline resistant, and was treated for diabetes foot ulcer.

A preferred composition is WF10 is disclosed in, e.g., U.S. Pat. No. 8,252,343 as an agent useful in treating allergies, asthma and dermatitis WF10.

WF10 is a sterile, pyrogen-free, 10% (w/v) aqueous dilute solution of the drug substance OXO-K993, which is analytically characterized as a solution containing the ions chlorite (4.25%), chloride (2.0%), chlorate (1.5%), sulfate (0.7%), and sodium (4.0%). Human clinical studies have generated substantial evidence of safety when WF10 is infused in a dose of 0.5 ml/kg per day for 5 consecutive days followed by a 16-day drug-free interval, constituting a "cycle". In two protocols, patients received 6 cycles of therapy and in another trial, patients received 4 cycles followed by maintenance use every 6 weeks for up to 128 weeks. In every case. WF10 showed an excellent safety profile with no steroid like side effects, no immune suppression, no antihistamine like side effects and no cardiovascular side effects.

WF10 has been shown to have an impact on macrophage function (M S. McGrath. C. Benike, F. W. Kuehne. E. Englemann: Effect of WF10 (TCDO) on antigen presentation. Transplant Proc. 30 (1998), 4200-4202) by stimulating phagocytosis and reducing the inflammatory phenotype (M S. McGrath, V. Kodelja: Balanced Macrophage Activation Hypothesis: A Biological Model for Development of Drugs Targeted at Macrophage Functional States. Pathobiology 67 (1999), 277-281). The evidence suggests that WF10 might down regulate immunologic activation through removal of the influence of inflammatory macrophages on chronic T cell activation.

However, no steroid like immune-suppressive effect and no anti-histamine like effect have been observed in studies on WF10. Rather an immune system normalization effect has been observed in in vitro studies (M. S. McGrath. J. O. Kahn. B. G. Herndier: Development of WF10, a novel macrophage-regulating agent. Curr. Opin. Investig. Drugs 3 (2002), 365-373).

Treatment of red blood cell dysfunction with WF10 is an unexpected new invention. It was unknown that red blood cell dysfunction could be the origin of diabetes associated pathologies called Syndrome X. It was thought that WF10 could cause hemolysis as in some DFU treated patients a transient drop in hematocrit had been observed after first infusion and blood transfusion was indicated. This transient drop in hematocrit was compensated by substantial erythropoesis and after 21 days hematocrit was back to baseline and after 3 months above baseline. Consequently in vitro and in vivo studies were conducted. It could be shown that WF10 does not cause hemolysis in healthy and HIV-infected individuals. In hyperglycemic patients and in patient with Thallassemia instead WF10 treatment induced a clearance of early/end glycation products and dysfunctional red blood cells at start of therapie and inactivates/scavenge immediately free hemoglobin and hemin (Kuehne, McGrath, unpublished data, Arnhold, personal communication).

The present invention provides a method of inhibiting/curing red blood cell disease/dysfunction, hemolytic anemia, hemorrhagic events, hemorrhagic bleeding with a therapeutically effective amount of WF10.

The present invention also provides a method for the inactivation/dimishing, termination, reduction of ongoing intra- and extracellular hemorrhagic events, hemorrhagic bleeding.

Examples of the types of symptoms described above may include, but are not limited to, the following: a patient has strong bleeding in the upper intestine/bladder and the urine is deep red. After the first infusions the bleeding symptoms had disappeared, the morning urine was yellow.

It will be understood from the description, and the examples provided, that chlorite. e.g., WF10, may be administered in symptom free diabetes patients to prevent the re-occurrence of hemorrhagic symptoms, in patients with mild hemolytic symptoms, or even in patients with moderate to severe symptoms. In diabetes patients having part of Syndrome X the drug might be administered to prevent reoccurrence or to stabilize symptoms, i.e. kidney function.

Chlorite is preferably administered to the subject intravenously. Chlorite may be co-administered or combined with all currently used anti-diabetes medication. These medications include metformin, sulfurylurea, and insulin. Chlorite may also be administered as monotherapy.

One embodiment of the invention is the administration of one treatment cycle of chlorite triannually, semi-annually, annually or bi-annually. In one embodiment, a dose of 0.5 ml/kg body weight is administered daily over 5 days as a treatment cycle of infusions. In one example, WF10 is diluted for use with normal saline or dextrose in water and is ideally used within 4 hours of preparation. Refrigerator or freezer storage is not recommended to extend the 4-hour limit. For example, chlorite, e.g., WF10 can be administered as a dose of 0.5 mL/kg of body weight, diluted into at least 250 mL of normal saline and infused over 60-90 minutes. For ease of administration, a standard dose of 50 to 75 mL may be administered to adults, regardless of the body weight. Depending on the individual medical need, the dose may be reduced to 0.375, or even 0.1 ml/kg, or as 5 to 50 mg per individual. In young children or sensitive persons on one hand, and in very severely affected or resistant patients on the other hand, the dose may be further adjusted within the range of 0.01 to 2 ml/kg. The dose adjustment is to be performed according to the individual medical need and in line with the decision of the physician prescribing the treatment.

In a further embodiment, the chlorite has a concentration of about 40 to about 80 mMol of $ClO_2$ per liter. In another embodiment, the chlorite has a concentration of about 60 mMol $ClO_2$ per liter.

In one embodiment, an infusion pump may be used for the administration of chlorite. In one embodiment, infusions are administered daily on consecutive days (for example each day for 5 consecutive days), but it is also possible to administer the drug every other day or to prolong the breaks between infusions to 2 or 3 days, accommodating weekends and holidays without interference with the pharmacological effect. In one embodiment, one cycle constitutes 5 infusions. However, since good effects have been seen after 2 to 3 infusions, the treatment may also consist of a short cycle of 2 or 3 or 4 infusions. In individual cases, a single infusion may be sufficient.

In one embodiment, the administration of chlorite to a subject may consist of 1 to 6 daily infusions within a 7 to 28 day period, or alternatively within a 7 to 21 day period or within a 7 to 14 day period. In another embodiment the administration of chlorite to a subject may consist of 2 to 5 daily infusions within a 7 to 28 day period, or within a 7 to 21 day period or within a 7 to 14 day period. Alternatively, the administration of chlorite to a subject may consist of 3 to 5 daily infusions within a 7 to 28 day period, or alternatively within a 7 to 21 day period or within a 7 to 14 day period. Alternatively, the administration of chlorite to a subject may consist of 4 to 5 daily infusions within a 7 to 28 day period, or within a 7 to 21 day period or within a 7 to 14 day period.

In another embodiment, the administration of chlorite to a subject may consist of 1 to 6 daily infusions within a 7 day period. Alternatively, within the 7 day period, the chlorite may be administered to the subject as 2 to 5 daily infusions or alternatively as 3 to 5 daily infusions or 4 to 5 daily infusions.

While the cycles may be repeated as frequently as every 2 to 3 weeks, the treatment interval may be triannually, semi-annually, annually or bi-annually. The treatment interval for each cycle may be adjusted to meet the individual symptoms. A single course will be sufficient to reduce the symptoms for a prolonged period, but in severely affected individuals, two or three cycles spaced every 2 to 4 weeks may be necessary to suppress or largely reduce hyperglycemia. As soon as a good therapeutic effect is reached after normalizing HbA1c values, no further cycles are needed until increase of HbA1c above 7.5%, which may be after 120 days or 240 days, or even later. Alternatively, to prevent the re-occurrence of HbA1c abobe 6.5%, the treatment may be repeated more often.

Preparation

Chlorite ionic solutions are commercially available or can be readily prepared by one of ordinary skill in the art. For example, tetrachlorodecaoxide (OXO-K993) can be used to prepare WF10 as follows.

1. WF10: Description of Manufacturing Process

Manufacturing Instructions for 200 L

Production Method: Filling of solution by aseptic processing using sterile filtration.

Weighing of Starting Materials

Weigh 20.0 kg* of OXO-K993 into the stainless steel container, close the container and transfer the product to the bulk production room.

*This quantity of OXO-K993 relates to a content of 100%. The exact amount has to be calculated according to the quantitative determination of OXO-K993 used for production (95 to 105%).

Manufacture of the Bulk Solution

Add approximately 160 kg of Water for Injection (WFI) into the manufacturing vessel and switch on the stirrer. Add the OXO-K993 to the vessel containing the WFI. Add the remaining purified water to make up to 200 L (=201.8 kg) of WF10 solution. Close the vessel and stir the bulk solution for 30 minutes.

In-Process Control and Release of the Bulk Solution

The QCU conducts the following in-process controls:

TABLE 1

In-process controls and specifications for the bulk solution

| Test | Method described in | Dilution [%]* | Specification |
|---|---|---|---|
| Appearance | ADS WF10.05 | 100 | Clear solution, no visible particles |
| Color | ADS WF10.05 | 100 | colorless (≤yellow 7) solution |
| Odor | ADS WF10.05 | 100 | odorless solution |
| pH-value | ADS WF10.05 | 20 | 10.75 to 11.9 |
| Osmolality | ADS WF10.05 | 100 | 290 to 330 mosmol/kg |
| rel. Densitiy $d_{20}^{20}$ | ADS WF10.05 | 100 | 1.004 to 1.013 |
| UV-spectroscopy Wavelength $\lambda_{max}$ Absorption $A_{260}$ | ADS WF10.05 | 20 | 258 to 262 nm 1.82 to 2.10 |
| Assay of chlorite by Iodometry | ADS WF10.05 | 100 | 97 to 103% |
| Bioburden | Ph. Eur. | 100 | ≤10 KBE/100 mL |

*Specification refers to indicated/tested dilution

Filtration of the Bulk Solution

After release by the QCU, the bulk solution is filtered through a 0.22 μm membrane filter into a previously sterilized stainless steel holding tank using nitrogen overpressure (>0.5 bar). The quantity of the filtered solution is checked and the holding tank transferred to the sterile manufacturing area. The filter is tested for integrity.

Sterile Filling of the Vials

The vials (Type I glass, 20R) are washed by an industrial bottle washing machine using water for injection, thereafter heated to 375° C. in a sterilization/depyrogenating tunnel. The holding tank containing the sterile filtered WF10 solution is aseptically connected to the online-filtration unit (using a 0.22 μm membrane filter) which is—via a tube—connected to the automatic filling machine. After discarding of the first 50 vials, the solution is filled under aseptic conditions into the 20-mL vials. Immediately after filling each vial is closed with a steam-sterilized 20 mm red chlorobutyl rubber stopper and sealed with a sterilized aluminum seal.

During the filling process, the filling volume of 2 bottles is determined at the beginning, each hour, and at the end [Limit: 20.0 to 22.0 mL].

The filled vials are removed from the sterile area and transferred in closed boxes to the packaging area.

The filter is tested for integrity.

Final Control of the Filled Vials

The QCU conducts the controls as shown in the following table.

TABLE 2

Final controls and specifications for filled vials

| Test | Method described in | Dilution [%]* | Specification |
|---|---|---|---|
| Appearance | ADS WF10.05 | 100 | clear solution |
| Color | ADS WF10.05 | 100 | colorless (≤yellow 7) solution |
| Odor | ADS WF10.05 | 100 | odorless solution |
| pH-value | ADS WF10.05 | 20 | 10.75 to 11.9 |
| Osmolality | ADS WF10.05 | 100 | 290 to 330 mosmol/kg |
| UV-spectroscopy Wavelength $\lambda_{max}$ Absorption $A_{260}$ | ADS WF10.05 | 20 | 258 to 262 nm 1.82 to 2.10 |
| Assay by Iodometry Equivalent to chlorite content | ADS WF10.05 | 100 | 95 to 105% 4.038 to 4.463 mg/mL |
| Sterility test | Ph. Eur./USP | 100 | sterile |
| Bacterial Endotoxin | Ph. Eur./USP | 100 | ≤10.00 IU/mL |
| Particulate matter (subvisible) | Ph. Eur./USP | 100 | ≤6000 particles ≥10 μm ≤600 particles ≥25 μm |
| 100% optical control: visible particles, cap, stopper, fissures, breakage, filling height, other irregularities; yield of vials | Ph. Eur./USP; internal procedures | — | Particles: essentially free other parameters: internal |

*Specification refers to indicated/tested dilution

2. NRI-1025: Description of Manufacturing Process

Manufacturing Instructions for 100 L

Production Method: Filling of solution by aseptic processing using sterile filtration.

Weighing of Starting Materials

Weigh 2,280.0 g* of sodium chlorite solution 25% into a suitable container.

This quantity of sodium chlorite relates to a content of 25%. The exact amount has to be calculated according to the quantitative determination of sodium chlorite solution used.

Weigh 440.0 g of sodium chloride into a suitable container.

Weigh 69.0 g of sodium carbonate (anhydrous) into a suitable container.

Weigh 40.0 g of sodium hydroxide (solid) into a suitable container.

Close the containers and transfer them to the bulk production room.

Manufacture of the Bulk Solution

Add approximately 70 kg of Water for Injection (WFI) into the manufacturing vessel and switch on the stirrer. Add successively sodium chloride, sodium carbonate, and sodium hydroxide to the vessel containing the WFI. Stir for 10 minutes and then add under stirring the sodium chlorite solution. Add the remaining WFI to make up to 100 L (about 100.9 kg) of NRI-1025 solution. Close the vessel and stir the bulk solution for at least 10 minutes.

In-Process Control and Release of the Bulk Solution

The QCU conducts the following in-process control:

TABLE 3

In-process controls and specifications for the bulk solution

| Test | Method described in | Dilution [%]* | Specification |
|---|---|---|---|
| Appearance | ADS NRI1025.00 | 100 | Clear solution, no visible particles |

TABLE 3-continued

In-process controls and specifications for the bulk solution

| Test | Method described in | Dilution [%]* | Specification |
|---|---|---|---|
| Color | ADS NRI1025.00 | 100 | colorless (≤yellow 7) solution |
| Odor | ADS NRI1025.00 | 100 | odorless solution |
| pH-value | ADS NRI1025.00 | 20 | 10.75 to 11.9 |
| Osmolality | ADS NRI1025.00 | 100 | 290 to 330 mosmol/kg |
| UV-spectroscopy | ADS NRI1025.00 | 20 | |
| Wavelength $\lambda_{max}$ | | | 258 to 262 nm |
| Absorption $A_{260}$ | | | 1.82 to 2.10 |
| Absorption $A_{360}$ | | | ≤0.05 |
| Bioburden | Ph. Eur. | 100 | ≤10 CFU/100 mL |

*Specification refers to indicated/tested dilution

Filtration of the Bulk Solution

After release by the QCU, the bulk solution is filtered through a 0.22 μm membrane filter into a previously sterilized stainless steel holding tank using nitrogen overpressure (>0.5 bar). The quantity of the filtered solution is checked and the holding tank transferred to the sterile manufacturing area. The filter is tested for integrity.

Sterile Filing of the Vials

The vials (Type I glass, 20R) are washed by an industrial bottle washing machine using water for injection, thereafter heated to 375° C. in a sterilization/depyrogenating tunnel. The holding tank containing the sterile filtered NRI-1025 solution is aseptically connected to the online-filtration unit (using a 0.22 μm membrane filter) which is—via a tube—connected to the automatic filling machine. After discarding the first 50 vials, the solution is filled under aseptic conditions into the 20-mL vials. Immediately after filling each vial is closed with a steam-sterilized 20 mm red chlorobutyl rubber stopper and sealed with a sterilized aluminum seal. During the filling process, the filling volume of 2 bottles is determined at the beginning, each hour, and at the end [Limit: 20.0 to 22.0 mL].

The filled vials are removed from the sterile area and transferred in closed boxes to the packaging area.

The filter is tested for integrity.

Final Control of the Filled Vials

The QCU conducts the controls as shown in the following Table 2.

TABLE 4

Final controls and specifications for filled vials

| Test | Method described in | Dilution [%]* | Specification |
|---|---|---|---|
| Appearance | ADS NRI1025.00 | 100 | clear solution |
| Color | ADS NRI1025.00 | 100 | colorless (≤yellow 7) solution |
| Odor | ADS NRI1025.00 | 100 | odorless solution |
| pH-value | ADS NRI1025.00 | 20 | 10.75 to 11.9 |
| Osmolality | ADS NRI1025.00 | 100 | 290 to 330 mosmol/kg |
| UV-spectroscopy | ADS NRI1025.00 | 20 | |
| Wavelength $\lambda_{max}$ | | | 258 to 262 nm |
| Absorption $A_{260}$ | | | 1.82 to 2.10 |
| Absorption $A_{360}$ | | | ≤0.05 |
| Assay by Iodometry Equivalent to chlorite content | ADS NRI1025.00 | 100 | 95 to 105% 4.038 to 4.463 mg/mL |
| Sterility test | Ph. Eur./USP | 100 | sterile |
| Bacterial Endotoxin | Ph. Eur./USP | 100 | ≤10.00 IU/mL |
| Particulate matter (subvisible) | Ph. Eur./USP | 100 | ≥10 μm: ≤6000; ≥25 μm: ≤600 particles/vial |
| 100% optical control: visible particles, cap, stopper, fissures, breakage, filling height, other irregularities; yield of vials | Ph. Eur./USP; internal procedures | — | Particles: essentially free other parameters: internal |

*Specification refers to indicated/tested dilution

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 62/207,774, filed Aug. 20, 2015, are incorporated by reference herein.

What is claimed:

1. A method for treating hemolytic anemia or smoldering hemolytic anemia that is caused by erythrocyte glycation, in a patient who has been diagnosed as being in need of treatment for such hemolytic anemia, wherein the method comprises administering to the patient an effective amount of a pharmaceutical composition comprising $ClO_2^-$.

2. The method according to claim 1, wherein the pharmaceutical composition comprises chlorite, chloride, chlorate, sulfate and sodium ions.

3. The method according to claim 1, wherein the pharmaceutical composition is WF10 comprising 10% tetrachlorodecaoxide.

4. The method according to claim 1, wherein the pharmaceutical composition comprises 4.25% chlorite, 2.0% chloride, 1.5% chlorate, 0.7% sulfate and 4.0% sodium ions.

5. The method according to claim 1, wherein the composition is administered intravenously.

6. The method according to claim 1, wherein the method further comprises evaluating the patient's HbA1c levels before said treatment and also at a time from 4 weeks to 8 weeks after said treatment.

7. The method according to claim 1, wherein said method reduces the risk of microvascular disease in the patient.

8. The method according to claim 7, wherein the pharmaceutical composition comprises chlorite, chloride, chlorate, sulfate and sodium ions.

9. The method according to claim 7, wherein the pharmaceutical composition is WF10 comprising 10% tetrachlorodecaoxide.

10. The method according to claim 7, wherein the pharmaceutical composition comprises 4.25% chlorite, 2.0% chloride, 1.5% chlorate, 0.7% sulfate and 4.0% sodium ions.

11. The method according to claim 7, wherein the composition is administered intravenously.

12. The method according to claim 1, wherein the method clears dysfunctional erythrocytes from the blood of the patient.

13. The method according to claim 12, wherein the pharmaceutical composition comprises chlorite, chloride, chlorate, sulfate and sodium ions.

14. The method according to claim 12, wherein the pharmaceutical composition is WF10 comprising 10% tetrachlorodecaoxide.

15. The method according to claim 12, wherein the pharmaceutical composition comprises 4.25% chlorite, 2.0% chloride, 1.5% chlorate, 0.7% sulfate and 4.0% sodium ions.

16. The method according to claim 12, wherein the composition is administered intravenously.

17. The method according to claim 1, wherein said method clears hemolytic products, resulting from hemolysis of erythrocytes, from the patient.

18. The method according to claim 17, wherein the pharmaceutical composition comprises chlorite, chloride, chlorate, sulfate and sodium ions.

19. The method according to claim 17, wherein the pharmaceutical composition is WF10 comprising 10% tetrachlorodecaoxide.

20. The method according to claim 17, wherein the pharmaceutical composition comprises 4.25% chlorite, 2.0% chloride, 1.5% chlorate, 0.7% sulfate and 4.0% sodium ions.

21. The method according to claim 17, wherein the composition is administered intravenously.

22. The method, according to claim 1, wherein, prior to treatment, the patient has an HbA1c level of 8 or above and, after the treatment, the HbA1c level is 6 or lower.

23. The method, according to claim 1, wherein the patient is not being treated for a diabetic foot ulcer.

* * * * *